(12) United States Patent
Heimann et al.

(10) Patent No.: US 7,932,354 B2
(45) Date of Patent: Apr. 26, 2011

(54) PROCESS FOR THE PRODUCTION OF COLLAGEN MATERIAL

(75) Inventors: Lydia Heimann, Hoesbach (DE); Elvira Dingeldein, Dreieich (DE); Michael Voges, Hoechst (DE); Ellen Schubert, Woerth (DE)

(73) Assignee: aap Biomaterials GmbH (DE)

( * ) Notice: Subject to any disclaimer, the term of this patent is extended or adjusted under 35 U.S.C. 154(b) by 127 days.

(21) Appl. No.: 12/399,607

(22) Filed: Mar. 6, 2009

(65) Prior Publication Data
US 2009/0227773 A1  Sep. 10, 2009

(30) Foreign Application Priority Data

Mar. 7, 2008  (DE) .......................... 10 2008 013 091
Jul. 1, 2008  (DE) ..................... 20 2008 008 627 U

(51) Int. Cl.
*A61K 38/17* (2006.01)
(52) U.S. Cl. ...................................................... 530/356
(58) Field of Classification Search ........................ None
See application file for complete search history.

(56) References Cited

U.S. PATENT DOCUMENTS

| | | | | |
|---|---|---|---|---|
| 3,949,073 A | * | 4/1976 | Daniels et al. | 514/17.2 |
| 4,795,467 A | * | 1/1989 | Piez et al. | 424/423 |
| 7,064,187 B2 | * | 6/2006 | Stone | 530/355 |

* cited by examiner

*Primary Examiner* — Suzanne M. Noakes
(74) *Attorney, Agent, or Firm* — DeMont & Breyer LLC

(57) ABSTRACT

The invention relates to a process for the production of a collagen implant for wound covering, in which a suspension comprising a telopeptide-containing collagen is produced and a phosphate buffer is added. An areal structure is produced by drying the collagen-containing mixture produced.

10 Claims, No Drawings

PROCESS FOR THE PRODUCTION OF COLLAGEN MATERIAL

FIELD OF INVENTION

The invention relates to a process for the production of collagen material, especially in the form of a spongy and/or fleece-like body, a collagen material produced in accordance with the process, and the use of the collagen material produced in accordance with the process.

BACKGROUND OF THE INVENTION

Collagen is the structural protein of connective tissue in fibrous form. A distinction is made between collagen of types I, II, III, X, etc., as a function of the structure, pharmacological action, and type of origin. Collagen fibers or fibrils are substantially obtained from comminuted Achilles tendons or from the subcutaneous tissue of cattle and horses. Due to the continuing problems with BSE, today collagen of bovine origin is practically no longer used. Collagen is obtained by gentle hydrolysis. It is a high molecular weight protein and a physiological substance.

The raw material obtained according to the known process goes through different cleaning and preparation steps and is finally usually lyophilized, and the final product accumulates in the form of highly porous, fibrous plates that are marketed in the size of a few square centimeters (e.g., 5×5, 5×10, 10×10 cm) with a thickness of ca. 3-6 mm and a weight of ca. 50-250 $g/m^2$, preferably 70-130 $g/m^2$.

Sterilization usually takes place by treatment with γ-rays. Commercial collagen sponges usually also contain an antibiotic for the prophylaxis of infection, with gentamicin but also vancomycin being used in particular. The gentamicin content is, for example, 1.3 mg base, corresponding to 2 mg sulfate per $cm^2$. In order to improve the stability of the sponges, which collapse, swell, and dissolve in the wet state, crosslinking of the fibers is carried out, if necessary, by a chemical treatment with, e.g., glutaraldehyde or formaldehyde.

However, this treatment is not harmless from a toxicological viewpoint. Furthermore, it adversely affects the hemostyptic action and reduces resorption. Resorption takes place by the activity of migrating macrophages and by collagenases. Different half-lives are determined by the solubility behavior as a function of the degree of crosslinking. In an animal experiment a resorption time of greater than 40 days was observed after s.c. implantation of bovine collagen (sponges) in rats. In bone surgery in rabbits the resorption time was greater than 3-6 weeks (Monograph: Collagen, Animal Origin, Bundesanzeiger No. 149, Aug. 10, 1994). Basically, the collagen resorption is influenced by the site of application, by the amount and type of the collagen implant, as well as by the natural or aldehyde crosslinking that is present.

Substantial areas of clinical application for collagen sponges are, among others, wound overlays for local hemostasis, the coating of tissue defects, skin replacement in the case of lesions, skin covering in the case of large-area burns, the filling of bone defects, e.g., after cystectomies, even in the jaw region.

The hemostyptic (hemostasis) characteristics of the collagen (type I) obtained from animal skin are explained by the contact of the blood platelets with the native triple-helical structure of the collagen with simultaneous activation of blood coagulation. The fibril structure of the native collagen and its polar molecular structure are essential for platelet aggregation. Porcine material, namely, pigskin (e.g., DD 233 785 A1 and DD 292 840 A5) has already been described as the initial raw material for processes for the production of such collagen products determined as hemostyptics.

Known hemostyptics of native collagen usually have a very low pH, typically less than pH 6. As a consequence, wound healing problems can occur.

On the other hand, European patent EP 428541 B1 shows the production of a collagen implant with a higher pH. For this, an oxygen buffer is added. However, no native collagen starting material but rather an atelocollagen is used for the production of the collagen implant. In distinction to native collagen starting substances, atelocollagens are readily soluble and not sensitive at greater than pH 6.5 in further processing. In spite of the high pH, an atelocollagen solidifies relatively simply. In the processing of native collagen, on the other hand, the acid stabilizes the collagen structure, probably by denaturing the protein strands. In the case of a rather high pH this effect no longer occurs, so that the structure decomposes. In comparison to telopeptide-containing collagen, that is collagens in which the telopeptides were not chemically removed, atelocollagens have lesser hemostatic action. Furthermore, implants produced from atelocollagens are as a rule brittle in the dry state and have little resistance to bending. On the other hand, in the wet state the implants produced from atelocollagens are as a rule no longer dimensionally stable and have only a very low resistance to tearing so that once a collagen implant becomes wet it can no longer be withdrawn from the wound and moved.

In spite of their frequent use in surgery and orthopedic and despite various changes in the production process carried out over the course of years, the products on the market that are primarily used for hemostasis after surgical interventions have significant disadvantages concerning their handling as well as their biological behavior.

Thus, it turns out in practice that the collagen materials, for example, in the form of sponges, often have too little water resistance, too long a resorption time, adhere to the surgical instruments and gloves, and bring about incompatibility phenomena, in which in part strong seroma formation and wound healing problems predominate.

Therefore, the water resistance is significant because immediately upon the application of the collagen materials they very rapidly receive tissue fluid and especially blood, therefore collapse and lose their spongy structure and rigidity. This has the consequence that the material can then no longer be correctly placed on wound surfaces and therefore corrections of position that are frequently necessary at the application site on the wound are no longer possible.

Furthermore, collagen materials often characteristically adhere to surgical instruments (scissors, clamps, forceps, etc.) or gloves as soon as they are wet, which makes correct, accurate placement on the wound extremely difficult. This characteristic proves to be extremely problematic and obstructive in particular in the more and more frequently practiced processes of minimally invasive surgery, since in these operations only a very small spatial freedom of mobility is given.

The long resorption time of ca. 20-40 days is a great disadvantage. The intended preferred application purpose, hemostasis, is namely achieved after a few minutes to hours and the actual purpose of the application is therewith achieved. Even the antibiotic added for the prophylaxis of infection is eluted very rapidly out of the collagen material, so that an antibiotic protection is ensured only for a few days. Accordingly, the collagen material is, rather, a danger in the case of a delayed bacterial colonization, since the antibiotic-free collagen can then serve in the wound as a nutrient medium for infectious pathogens, especially when the wound must be drained on account of a heavy secretion. Therefore, for these reasons a much shorter dwell time (resorption time) of the collagen material would be extremely desirable.

However, the decisive medical disadvantage of the commercial collagen materials is based on the frequently observed, partially very pronounced incompatibility phenomena. After application these phenomena rapidly lead to inflammatory processes with cellular necroses and a strong secretion (seroma formation) that disturbs and greatly delays the susceptible natural healing process. This frequently prevents regular wound closure. These phenomena have the result more and more frequently that surgeons and orthopedists do not use the actually desired and indicated usage of collagen materials since the described side effects cannot be accepted from a medical viewpoint and also a disturbed and delayed wound healing course should not be expected of the patient.

SUMMARY OF THE INVENTION

The invention has the basic problem of indicating an especially economical process for the production of a collagen material, in particular in the form of a spongy and/or fleece-like body that is significantly better, when possible, in its simpler and more reliable application and handling, distinctly shorter resorption time, and compatibility than the currently available products. That is, the collagen material that is to be newly developed should display a good hemostyptic action, an improved water resistance, be easier to handle and apply, not adhere to instruments and the like, have a shorter resorption time, and have significantly improved compatibility in order that it can be used in human and/or veterinary medicine and in particular for the covering of wounds or as an implant.

In particular, one problem of the invention is to make a collagen material available that is dimensionally stable and resistant to bending in the wet as well as in the dry state, and in any case has a slightly acidic pH.

The problem of the invention is solved by a process for the production of a collagen material as well as by a collagen-containing areal structure according to one of the independent claims.

Preferred embodiments and developments of the invention can be gathered from the particular subclaims.

According to the invention, on the one hand a process for the production of a collagen material, especially an implant for wound covering, is provided.

To this end a suspension is produced that comprises a telopeptide-containing collagen. Therefore, no chemically treated atelocollagen is used in which the telopeptide chains are for the most part removed and that dissolves relatively well in water.

Rather, a native collagen is preferably used for production, from which a collagen-containing suspension is produced, preferably with the addition of an acid. The collagen is therefore not dissolved but rather remains preserved in particulate form in the suspension.

A phosphate buffer is added to the suspension, as a result of which the suspension can already be adjusted to an approximately neutral pH.

The inventors found that the use of a phosphate buffer leads to a solidification of the collagen material. This solidification probably comes about by crosslinking of the collagen fibrils, for example, due to Van-der-Waals forces. For this, the suspension is allowed to stand until the crosslinking or solidification has sufficiently progressed.

Then, an areal structure can be produced by drying the collagen-containing mixture created. "Drying" denotes every procedure in which the water is removed and the collagen as well as other solids remain in the form of an areal structure.

The drying preferably takes place in the framework of a freeze-drying process in which, for example, the collagen-containing mixture is shock-frozen in flat dishes and then dried in a vacuum.

In a preferred embodiment of the invention the suspension is produced with the addition of phosphoric acid. As a result, the phosphate component of the mixture produced after the addition of the phosphate buffer is elevated, which elevates the strength of the areal structure produced.

The addition of the acid generally seems to lead at least to a swelling of the collagen, as a result of which collagen fibrils are formed, at least partially, that can crosslink with each other after the addition of the phosphate buffer.

In a preferred embodiment of the invention the suspension is adjusted to a pH between 5.5 and 8.5, preferably between 5.8 and 7.8, and especially preferably between 6.0 and 7.0 by the phosphate buffer.

It turned out that the wound healing noticeably deteriorated at less than pH 6.0. On the other hand, greater than pH 7.0 can result in changes, in particular of antibiotics. In particular, added gentamicins can form toxins.

A sodium hydrogen phosphate, in particular di- or tri-sodium hydrogen phosphate, is preferably used as a phosphate buffer. The sodium ions do not result, in contrast to the ions of other phosphates, in any undesired interactions with the tissue.

In a preferred embodiment of the invention a suspension with a collagen content of 0.3-7, preferably 0.5-3, especially preferably 0.6-1.5 wt % is produced. Before drying, the solids content of the mixture produced is between 0.2-10 wt %, preferably 0.3-8 wt %, and especially preferably 0.5-2.5 wt % in a preferred embodiment of the invention. The solids content is the amount of the solids remaining after drying the mixture.

The weight per unit area and the porosity of the material produced can be adjusted in particular via the collagen content of the suspension, the amount of collagen, and the solids content.

An areal structure can be made available with the invention that comprises a phosphate, especially a disodium hydrogen phosphate component of 80-500, preferably 100-400, and especially preferably 220-370 mg/g. The phosphate components in the cited range are especially tissue-compatible.

In a development of the invention the suspension is mechanically denatured, especially in a colloid mill. Such a mechanical denaturing in which only one acid is added has the result that the characteristics of the native collagen remain largely preserved, as a consequence of which in particular the hemostatic characteristics are improved over known atelocollagen implants.

Relatively thick areal structures with a thickness between 1 and 10 mm, preferably between 2 and 7 mm, and with a rather low weight per unit area, preferably between 20 and 200, especially preferably between 50 and 150 $g/m^2$, can be produced with the invention.

Thus, an areal structure can be made available that takes up at least three times, preferably at least five times, and especially preferably at least eight times its own weight of liquid, in particular of water.

Pig skins are preferably used as starting material for the production of the collagen material. In comparison to bovine or equine tissues, porcine collagens have better compatibility, in particular if they are not greatly changed chemically.

In a development of the invention, an antibiotic is added to the collagen material. In particular, an antibiotic such as gentamicin, especially gentamicin sulfate and/or phosphate,e is/are stirred into the suspension.

Gentamicin sulfate is a standard antibiotic with quite good compatibility. Compared to gentamicin sulfate, the addition of gentamicin phosphate has the advantage, however, that the phosphate concentration is elevated, as a result of which the strength of the areal material produced is improved. Thus, when gentamicin phosphate is used the amount of the phosphate buffer can also be reduced.

A porous areal structure that is stable when wet and also bend-resistant in the dry state can be made available with the invention that has a pH of greater than 5.8, preferably greater than 6.5, and especially preferably greater than 7.2. The pH of the areal structure in the sense of the invention is determined by impregnating the areal structure with deionized water and subsequent pH measurement.

Furthermore, especially good hemostasis is ensured by the fact that the areal structure comprises collagens that comprise telopeptides at least in part.

The amount of telopeptide-containing collagens is preferably greater than 40%, preferably greater than 60%, and especially preferably greater than 80%.

Preferably only native collagens are used to produce the collagen-containing areal structure. The collagen content of the areal structure is between 10 and 80, preferably between 20 and 60 wt %.

The areal structure has a wet tear resistance of greater than 0.05, preferably greater than 0.07, especially preferably greater than 0.1 N/mm$^2$. Thus, the implant in accordance with the invention can be removed and shifted even after having been placed on a wound.

Relative to a 1 cm wide strip of the areal structure, the wet tear resistance is greater than 0.5, preferably greater than 1.0, especially preferably greater than 1.5 N/cm.

DETAILED DESCRIPTION

A collagen-containing areal structure can be produced, for example, as follows:

Starting from a porcine starting material, pigskin is purified basically and oxidatively and subsequently adjusted to acidic with dilute phosphoric acid, after which the skin is washed, comminuted and mixed with water after intermediate chilling at −28±10° C. so that a homogeneous suspension with a collagen content of approximately 1% arises, the suspension is mixed, if necessary, with at least one antibiotic and the entire mixture then adjusted by the addition of a phosphate buffer to a neutral to slightly basic pH of preferably 6.5-8.5, especially preferably 7.2-7.8, the solids content is adjusted to 0.5-2.5%, and the mixture lyophilized (freeze-dried) after beginning or successful fibrillation of the suspension.

Thus, pigskin is used as starting material for the obtention of collagen in accordance with the invention so that on the one hand the BSE problems that exist for bovine raw materials can be reliably excluded. On the other hand, it is known that the biological characteristics of pig tissues, especially of pigskin, are closer to those of human organs, in particular of the skin, then bovine or equine tissue.

It is especially important in the process as regards the stability of the collagen material to be produced that the oxidative preparation of the pigskin does not take place in an acidic but rather in a neutral to basic environment. An oxidative treatment, in particular with hydrogen peroxide, after the acidic treatment has a negative effect on the fibrillation necessary for the stabilizing of the collagen material in the physiological pH range of 7.2-7.8, and is therefore performed before the acidic treatment.

It was furthermore found that the acid treatment with phosphoric acid is of decisive importance for the stability, in particular, however, for the adhesion of collagen to instruments and the like. Thus, in particular the lack of adherence to instruments in accordance with the invention can be surprisingly achieved in that, in the production process, the customarily performed hydrochloric acid treatment is replaced by the use of phosphoric acid.

It is furthermore significant that the skin is not mixed with water until after the intermediate chilling in order to adjust to a collagen content of approximately 0.5-3.5%. The collagen structure is namely damaged by an excess of water during the intermediate chilling, so that the desired stability is not achieved in the physiological pH range at the end of the production of collagen material. Therefore, the intermediate chilling is carried out in acids, preferably at pH 3.0±0.5.

For the improvement of the water resistance and elasticity of the collagen material, the higher pH of 5.5-8.5, preferably 6.0-8.0, especially preferably 6.3-7.7 by the phosphate buffering after the addition or especially preferably with the addition of the antibiotic proves to be positive, since better fibrillation could thereby be achieved.

An additional reinforcing of the crosslinking, for example by a mechanical treatment, especially a shaking treatment with subsequent standing for several hours, can be eliminated by mixing the suspension with the antibiotic in the form of a phosphate-buffered solution, preferably at pH 6.5-7.8.

The suspension with the antibiotic is advantageously used as phosphate solution; i.e., phosphate is used as the counterion of the antibiotic. Thus, interfering anions are no longer present in the suspension, as a result of which an additional reinforcement of the crosslinking, for example by a mechanical treatment, in particular a shaking treatment, with subsequent standing of several hours is unnecessary.

The pigskin used comes exclusively from young slaughtered animals 6-9 months old. They constitute a more homogeneous and thus biologically more valuable starting material than is the case with cattle or horses, which are only slaughtered at a greater age.

It surprisingly turned out in the preparation of the pigskin that the fat content of the starting material has an essential influence on essential characteristics of the final product, namely, among others, the elasticity, mechanical strength, and resorption. Therefore, subcutaneous tissue with a fat content of the dry skin of not greater than 2%, especially preferably 0.1-2%, more preferably 0.5-1.6%, is preferably used.

Moreover, it proved to be advantageous to carry out gassing with ethylene oxide instead of the customary sterilization of the final product with γ-rays, as a result of which the normal degree of crosslinking of the collagen fibrils can obviously be raised.

Plasma sterilization with hydrogen peroxide gassing is performed for an especially good crosslinking and stabilization of the collagen material.

In an advantageous configuration of the process, salt treatment stages with sodium chloride and sodium bicarbonate preceded basic and oxidative purification of the pigskin in order to achieve an especially gentle swelling of the skin. A pneumatic loosening of the collagen carried out in the state of the art, for example, according to document DD 233 785 A1, is not preformed in the present instance for reasons of an especially gentle treatment.

Moreover, in spite of the improved water resistance, the collagen materials produced in accordance with the invention surprisingly additionally displayed a substantially shorter resorption time in the animal experiment after implantation under the back skin of rats, in comparison to two commercial products.

The cited changes in the production process of the collagen material also surprisingly result in a comparatively improved hemostyptic action.

A totally unforeseeable result occurred in the changes carried out in accordance with the invention in the production process and the resulting systematic checking of different experimental productions in the animal experiment. It turned out that the pH of the collagen suspension is of decisive importance for the biological compatibility of the collagen material. Thus, pH 7-8 collagen materials were clearly more compatible than commercial sales products with a pH between 4 and 5 that were tested in parallel.

It turned out in the development work in this direction that collagen materials with a pH between 6.5 and 8.5, preferably 7.2-7.8, improved the compatibility in such a manner that no increased secretion (seroma formation) took place in the wound region, the skin wounds healed p.p., rapid wound closure took place, and physiological conditions corresponding to the proper healing course were to be found in the histological evaluation of tissue samples taken from the implantation site.

Examples for the production of collagen material in accordance with the process of the invention are indicated in the following that were then used as the basis for reference tests with commercial products.

Example 1

Split pigskins underwent salt treatment with sodium chloride and sodium bicarbonate and were purified by 24-h basic treatment with 2% sodium hydroxide and a 30 min oxidative treatment with 20% hydrogen peroxide solution. Rinsing with water preferably takes place between the individual treatment steps.

The skin pieces are subsequently adjusted to pH 2.5-3.5 with 0.2M phosphoric acid, washed, and comminuted (ground). The collagen pulp obtained is ground after intermediate chilling at −28±10° C. and mixed with water so that a homogenous suspension of approximately 1% collagen content is produced.

At first, a solution of gentamicin sulfate adjusted to pH 6.5 to 7.8 with a phosphate buffer, in particular a mixture of a di- and trisodium hydrogen phosphate solution, is added within 10 min.

Then, the entire suspension of homogenized collagen and gentamicin sulfate is adjusted to a neutral to slightly basic pH (pH 6.5-8.5) with the phosphate buffer and adjusted to a solids content of 0.5-2.5% with distilled water.

Thereafter, the suspension is slowly agitated further at a maximum of 25° C. until fibrillation begins.

Then, the suspension is poured into formative vessels and lyophilized (freeze-dried).

Example 2

Split pigskins underwent salt treatment with sodium chloride and sodium bicarbonate and were purified by 24-h basic treatment with 2% sodium hydroxide solution and a 30 min oxidative treatment with 20% hydrogen peroxide solution. Rinsing with water preferably takes place between the individual treatment steps.

The skin pieces are subsequently adjusted to pH 2.5-3.5 with 0.2M phosphoric acid, washed and comminuted (ground). The collagen pulp obtained is ground after intermediate chilling at −28±10° C. and mixed with water so that a homogenous suspension of approximately 1% collagen content is produced.

At first, an acidic solution (pH 4.5-5.5) of gentamicin sulfate is added to the suspension within 10 min.

Then, the entire suspension of homogenized collagen and gentamicin sulfate is adjusted to a neutral to slightly basic pH (pH 6.5-8.5) with a phosphate buffer, especially a mixture of a di- and trisodium hydrogen phosphate solution.

Thereafter, the suspension is adjusted to a solids content with regard to collagen of 0.5-2.5% (usually 1%) with distilled water.

Subsequently, the suspension is slowly agitated further at a maximum of 25° C. until fibrillation begins.

The suspension is then poured into formative vessels.

In order to reinforce the crosslinking the pulp is shaken with a suitable apparatus in lyophilizing dishes and allowed to stand at least 20 h at ca. 10° C. for completion of the fibrillation.

After successful fibrillation the suspension is lyophilized (freeze-dried).

Example 3

Split pigskins underwent salt treatment with sodium chloride and sodium bicarbonate and were purified by 24-h basic treatment with 2% sodium hydroxide solution and a 30 min oxidative treatment with 20% hydrogen peroxide solution. Rinsing with water preferably takes place between the individual treatment steps.

The skin pieces are subsequently adjusted to pH 2.5-3.5 with 0.2M phosphoric acid, washed, and comminuted (ground). The collagen pulp obtained is ground after intermediate chilling at −28±10° C. and mixed with water so that a homogenous suspension with a collagen content of approximately 1% is produced.

An aqueous 2% gentamicin sulfate solution is conducted through a column with a phosphate-charged anion-exchange resin until no more sulfate can be demonstrated in the eluate. The gentamicin phosphate solution obtained in this manner is then adjusted to pH 6.5-7.8 with a phosphate buffer, especially a mixture of a di- and trisodium hydrogen phosphate solution, and subsequently added to the collagen suspension within 20-30 min.

Then the entire suspension of homogenized collagen and gentamicin sulfate is adjusted to a neutral to slightly basic pH (pH 6.5-8.5) with the phosphate buffer.

The suspension is then adjusted to a solids content with regard to collagen of 0.5-2.5% (usually 1%) with distilled water.

The suspension is then slowly agitated at a maximum of 25° C. until fibrillation begins and is poured into formative vessels.

Since problematic sulfate ions are no longer present in the suspension, reinforcement of the crosslinking as described in Example 2 is no longer necessary.

After successful fibrillation the suspension is lyophilized (freeze-dried).

For evaluation of the characteristics and effects, a collagen material produced in accordance with the invention was compared with two commercially available products of different producers in animal experiments with rats, namely, 1. Collagen material, especially collagen fleece, produced in accordance with the invention, in particular according to Example 2:
   porcine collagen,
   pH 7.6,
   gentamicin content 1.3 mg base per cm²
2. Commercial product A:
   equine collagen,
   pH 4-5
   gentamicin content 1.3 mg base per cm².
3. Commercial product B:
   equine collagen,
   pH 4-5
   gentamicin content 1.3 mg base per cm².

With 5 rats per experimental period (5, 15, 35 days), two collagen material samples 1 cm² in size were implanted per animal paravertebrally right and left under the skin of the back. The healing course was checked daily by adspection. After the course of the experimental times the animals were sacrificed, the appropriate site together with skin, hypodermis, collagen material, and, if necessary, skin musculature was removed from the implantation side and histologically examined (light microscope).

Handling

The collagen material produced in accordance with the invention corresponded to the handling standards of surgeons, i.e., no adherence to instruments, gloves, etc., with firm adherence to the wound surface and more reliable and simpler application with good water resistance. In the reference products A and B, the known handling disadvantages (adherence to instruments and gloves, distinctly lesser water resistance) were observed.

Hemostasis

The very good hemostasis observed for the collagen material produced in accordance with the invention can be traced to the strong fibrillation during production. In comparison to a commercial product approved for hemostasis, the coagulation time was reduced to a third to a fifth.

Histology

The collagen material produced in accordance with the invention displays clearly better compatibility in comparison to commercial products A and B. Cells had already migrated into the center of the implants after 5 days, whereas in the reference products the implants were marginally colonized at most.

No cellular fragments and no necrotic cells (as in A and B) were observed in the implant itself.

After 15 days the collagen material produced in accordance with the invention was partially resorbed into the surrounding connective tissue and integrated. Products A and B could still be macroscopically recognized and were not appreciably resorbed.

After 35 days only marginal remnants could be histologically recognized in the implant produced in accordance with the invention. In implants A and B, the collagen materials are still largely preserved.

Healing Course

Distinct differences were seen even in the immediately postoperative healing course (compatibility). Thus, swellings occurred in products A and B that were not observed in the collagen material produced in accordance with the invention. Furthermore, in the case of this collagen material, after 5 days the wounds had firmly healed p.p. whereas in products A and B only the wound edges had adhered, and spread apart under light pressure. The intact implants were also underneath them whereas, in contrast thereto in the case of the collagen material produced in accordance with the invention, the implants could no longer be macroscopically recognized.

The described experimental results clearly show that the resorption time as well as in particular the histological compatibility of the different collagen-material implants are not influenced or only insignificantly influenced by the antibiotic content, but rather that possibly the type of collagen, in particular however the significant pH difference, are of decisive significance for the clearly better compatibility, good hemostyptic action, and greatly reduced resorption time of the collagen material produced in accordance with the invention.

The promotion of wound healing in the animal experiment by the physiological collagen material produced in accordance with the invention is based on stimulation of the cellular activity, especially fibroblast activity.

In the first clinical applications the collagen material produced in accordance with the invention showed, in comparison to known commercial products, as expected, a very much better and more rapid healing course without wound healing problems or seroma formation.

What is claimed is:

1. A process for the production of a collagen material, comprising:
   (a) producing an suspension comprising a telopeptide-containing collagen wherein said suspension has an acidic pH which has been adjusted by the addition of phosphoric acid;
   (b) adding a phosphate buffer to the suspension of step (b), resulting in a telopeptide collagen-containing mixture; and
   (c) drying the telopeptide collagen-containing mixture, thereby producing an areal structure.

2. The process of claim 1, wherein a native collagen is used to produce the suspension.

3. The process of claim 1, wherein mammalian skins are used as the collagen material.

4. The process of claim 1, wherein the collagen-containing mixture is adjusted to a pH between 5.5 and 8.5 by addition of the phosphate buffer.

5. The process of claim 1, wherein the suspension is produced with a collagen content of 0.3-7 wt %.

6. The process of claim 1, wherein before drying, the mixture is adjusted to have a solids content of 0.2-10%.

7. The process of claim 1, wherein the areal structure is produced with a disodium hydrogen phosphate component of 80-500 mg/g.

8. The process for the production of a collagen material in accordance with claim 1, wherein the suspension of step (a) is mechanically denatured.

9. The process of claim 1, further comprising adding an antibiotic.

10. The process of claim 3, wherein mammalian skins from pigs are used as the collagen material.

* * * * *